United States Patent
Tao et al.

(10) Patent No.: US 6,784,999 B1
(45) Date of Patent: Aug. 31, 2004

(54) SURFACE PLASMON RESONANCE DETECTION WITH HIGH ANGULAR RESOLUTION AND FAST RESPONSE TIME

(75) Inventors: Nongjian Tao, Phoenix, AZ (US); Salah Boussaad, Tempe, AZ (US); Wenlue Huang, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 10/031,659

(22) PCT Filed: May 16, 2000

(86) PCT No.: PCT/US00/13283

§ 371 (c)(1),
(2), (4) Date: Nov. 13, 2001

(87) PCT Pub. No.: WO00/70328

PCT Pub. Date: Nov. 23, 2000

Related U.S. Application Data
(60) Provisional application No. 60/134,482, filed on May 17, 1999.

(51) Int. Cl.[7] ............................................... G01N 21/00
(52) U.S. Cl. ..................................................... 356/445
(58) Field of Search ............................. 356/237.1, 445, 356/138, 448, 73

(56) References Cited

U.S. PATENT DOCUMENTS

| | | | |
|---|---|---|---|
| 4,997,278 A | | 3/1991 | Finlan et al. |
| 5,313,264 A | * | 5/1994 | Ivarsson et al. ............... 356/73 |
| 5,875,032 A | * | 2/1999 | Naya ........................... 356/445 |
| 5,986,762 A | | 11/1999 | Challener |
| 6,570,657 B1 | * | 5/2003 | Hoppe et al. ................ 356/445 |
| 6,577,396 B1 | * | 6/2003 | Naya ........................... 356/445 |

OTHER PUBLICATIONS

Caruso et al. "Acousto–optic surface–plasmon resonance measurements of thin films on gold", *J. Appl. Phys.* 83: 1023 (1998).

Kretschmann, E. "The ATR method with focused light–application to guided waves on a grating". *Optics Communications*, 26:41 (1978).

Liedberg et al., "Surface plasmon resonance for gas detection and biosensing", *Sensors and Actuators*, 4: 299 (1983).

* cited by examiner

*Primary Examiner*—Alan Mathews
(74) *Attorney, Agent, or Firm*—Marshall, Gerstein & Borun LLP (57) ABSTRACT

A device and method of detecting surface plasmon resonance for sensing molecules or conformational changes in molecules with high resolution and fast response time is disclosed. Light from a light source (14) is focused through a prism onto a metal thin film (15) on which sample molecules to be detected are adsorbed. The total internal reflection of the laser/incident light is collected with a differential position or intensity sensitive photo-detecting device instead of a single cell or an array of photo-detectors (12) that are widely used in previous works. The ratio of the differential signal to the sum signal of the differential position or intensity sensitive photo-detecting device (12) provides an accurate measurement of the shift in the surface plasmon resonance angle caused by the adsorption of molecules onto the metal films (15) or by conformational changes in the adsorbed molecules. The present invention requires no numerical fitting to determine the resonant angle and the setup is compact and immune to background light, The methods and sensors of this invention can be used in numerous biological, biochemical, and chemical applications such as measuring subtle conformational changes in molecules and electron transfer reactions can be studied.

37 Claims, 10 Drawing Sheets

SURFACE PLASMON RESONANCE DETECTION WITH HIGH ANGULAR RESOLUTION AND FAST RESPONSE TIME

CROSS REFERENCE TO RELATED APPLICATIONS

This application claims the benefit of U.S. Provisional Patent application Serial No. 60/134,482 filed May 17, 1999.

This invention was made with government support under Grant CHE9818073 awarded from the NSF, and Grant GM-08205 awarded from the NIH.

FIELD OF THE INVENTION

The present invention relates generally to methods and measuring instruments or sensors for use in biological, biochemical, and chemical testing, and particularly to methods, instruments, and the use of instruments which utilize surface plasmon resonance (SPR) for detecting molecules or monitoring structural and electronic changes in the molecules with ultra-high resolution and ultra-fast response times.

BACKGROUND OF THE INVENTION AND PRIOR ART

Surface plasmon resonance (SPR) is the oscillation of the plasma of free electrons which exists at a metal boundary. These oscillations are affected by the refractive index of the material adjacent the metal surface. It is this phenomenon that is used to detect minute changes in the refractive index of a surface and forms the basis of various sensor mechanisms. Surface plasmon resonance spectroscopy has emerged as a powerful technique in recent years for detection and analysis of chemical and biological substances in many research areas and industrial applications, such as surface science, biotechnology, environment, drug and food monitoring, and medicine. In biological sensors, detection of antibodies and their reactions with antigens using SPR is of primary interest in biomedical diagnostics, where the presence of antibodies associated with a bacteria or virus is an important indication of infection. SPR has also been applied to gene probes where deoxyribonucleic acid (DNA) or ribonucleic acid (RNA) binding to a defined sequence in target analytes can be employed. In addition, SPR has found applications in detecting trace amount of toxic agents in air or in water for environmental protection or for chemical/biological warfare alert. Finally, SPR-based sensors are promising in food industry for detecting chemical and biological contamination in food. In all these application, improving the resolution and time response of SPR detection is of vital importance.

Surface plasmon resonance may be achieved by using the evanescent wave which is generated when a p-polarized light beam is totally internally reflected at the boundary of a medium, e.g. a glass prism, which has a high dielectric constant. A paper describing the technique has been published under the title "Surface plasmon resonance for gas detection and biosensing" by Lieberg, Nylander and Lundstrom in Sensors and Actuators, Vol. 4, page 299. The widely used methods for detecting SPR are based on attenuated total reflection (ART) of a collimated laser beam is incident on a glass body, usually a prism, on which a thin metal film is coated. When the incident light reaches an appropriate angle the reflection decreases sharply to a minimum, corresponding to the excitation of surface plasmon waves in the film. The total internal reflection is detected with a photo-detector as a function of incident angle which is varied by rotating the prism. The photo detector is also rotated in order to catch the reflected light. When the incident beam reaches an appropriate angle, the reflection decreases sharply to a minimum that appears as a dip in the reflectivity vs. incident angle plot. The angular resolution achieved by this rotating prism approach is typically $10^{-2}$–$10^{-3}$ deg (degrees), limited by errors in the angular position and noise in the intensity of the reflected light. For comparing different SPR detection techniques, the SPR resolution is often described in terms of the smallest detectable change in the refractive index for an analyte [refractive index units (RIU)]. The above angular resolution corresponds to $10^{-5}$–$10^{-6}$ RIU at a wavelength of 630 nm. For higher angular resolutions, a large distance between the prism and the photodetector is required which makes the setup not only bulky but also more susceptible to mechanical noise and thermal drift. The response time is slow because of the mechanical movements in the setup.

Mechanical movements can be avoided by fixing the photodetector at an angle near resonance and measuring the intensity change in their reflection due to SPR angular shift. A major advantage of this approach is that the response time is only limited by the photodetector and the associated electronics which can be as fast as nanoseconds. A drawback, however, is that the relationship between the intensity and the sensitivity of the resonance angle measurement is dependent on the angle at which the photodetector is fixed. Major limitations in the resolution of the method come from fluctuation in the intensity of the laser and from thermal and mechanical drift in the setup.

Another widely use ATR-based method also fixes the position of the prism and replaces the collimated incident light in the above setups with a fixed convergent beam that covers a range of incident angles. This method is generally disclosed in "The ATR method with focused light—application to guided waves on a grating" by E. Kretschmann, Vol. 26, number 1, Optics Communications, 1978, and in U.S. Pat. No. 4,997,278 by Finaln et. al. The reflections from different incident angles are collected simultaneously with a linear diode array (LDA) or charge coupled device (CCD) detector. This method involves no mechanical movements, but simultaneous detection of many channels (e.g., 1024 in a typical LDA) slows down the response time. The typical angular resolution is $10^{-2}$–$10^{-3}$ deg or $10^{-5}$–$10^{-6}$ RIU. As in the method with a rotating prism, high angular resolution of this method requires a large distance between the prism and the photodetector.

The above setups involve reflection intensity versus incident angle (an angle-scan system); SPR has also been detected by modulating the wavelength of incident light as described by Caruso, F., et al. (J. Appl. Phys., 1998, 83, 1023). The wavelength modulation causes modulation in the reflection intensity which is monitored with a lock-in amplifier and provides an accurate measurement of the SPR dip position. Using an acousto-optic tunable filter (AOTF), it was demonstrated that a wavelength change of 0.0005 nm, corresponding to $5 \times 10^{-7}$ RIU at a wavelength of 630 nm, can be detected. When applied to DNA-SH adsorption on gold, the signal to noise ratio of the AOTF SPR is six times better than that achieved by an angle-scan system.

As mentioned above, these methods suffer two major drawbacks: slow response time and limited angular resolution. The former one prevents the methods from detecting a fast process, such as the initial adsorption process of molecules onto surfaces, gas interactions, reactions between surface bound molecules and molecules in solution, and fast conformational changes in adsorbed proteins. The later one limits the sensitivity of SPR for detecting small amounts of molecules or small structural or conformational changes in molecules. In the first method, the response is slow because of mechanical movements involved in the method. The second method has no mechanical movements, but simultaneously detecting may channels (e.g., 1024 in a typical linear diode array) slows down the response time. For both methods, the angular resolution is typically poorer than $10^{-3}$ degrees (typically on the order of $10^{-2}$). For high angular resolution, both methods require a large distance between the sample and the detector, which makes the setups more susceptible to mechanical noise and thermal drift. Large distances, however, deteriorate the quality of the detected beam and makes to the SPR instruments bulky. For a given sample-detector distance, the resolution of the first method is limited by the precision of measuring the angular position of the prism. The resolution of the second method is limited by the number of channels (pixels) in the photo detector array and the noise level in the measured intensity in each channel. Improved resolution can be obtained using a software routine to fit the data collected by either the first or the second methods, however, this fitting procedure requires extra time and its reliability depends on the accuracy of each data point measured. The second method suffers an additional problem, in that the intensity of the beam is spread out over many channels, which decreases the signal to noise ratio, and therefore limits the resolution.

The present invention discloses a new SPR detection method that achieves an angular resolution in the order of $10^{-5}$ deg (or $10^{-8}$ RIU) and response times in the range of 1 μs. The method has several additional features which include simplicity, good linearity, compactness, and immunity to ambient light. The method uses a convergent beam focused onto a thin metal film, but the total internal reflection is collected by a differential position or intensity sensitive photo-detecting device instead of a CCD or a LDA. The reflected light falling on the cell(s) of the differential position or intensity sensitive photo-detecting device is first balanced so that the SPR dip is located near the center of the differential position or intensity sensitive photo-detecting device. Because the differential signal is linearly proportional to the shift in the SPR angle and can be easily amplified without saturation problem, it provides an accurate detection of SPR. We note that a big-cell differential position sensitive photo-detecting device has been used by Alexander, S. Et al., (J. Appl. Phys. 1989, 65, 164) in the atomic force microscope (AM) in which the deflection of a laser beam due to bending of the AM cantilever is measured. In the present application it is the intensity distribution due to a SPR angular shift rather than physical movement of the laser beam that is measured.

SUMMARY OF THE INVENTION

The present method is carried out by focusing a diode laser through a prism onto a transparent plate coated with a thin metal film. The transparent plate is supported on an optical prism with index of refraction matching substance. The incident light and the differential position or intensity sensitive photo-detecting device are adjusted so that the SPR dip in the total internal reflection is located in the middle of the photo cells of the photodetecting system, corresponding to a zero differential signal from cell(s). On the metal film, a sample cell with necessary electrodes for controlling the electrochemical potential of the metal film is mounted into which molecules to be detected or studied or introduced. The presence of molecules or changes in the molecules on the metal film leads to a small shift in the SPR dip and results in a change in the differential signal of the differential position or intensity sensitive photo-detecting device that is easily amplified and detected.

One aspect of the present invention is to create a method of and sensor for detecting SPR for biological, biochemical, and chemical applications with a higher angular resolution and a faster response time. The angular resolution and speed of response is improved by being able to precisely position a differential position or intensity sensitive photodetecting device such that is centered on and detects the exact dip corresponding to surface plasmon resonance. Thus the detecting device can monitor changes with a response time of a few microseconds and angular resolutions on the order of $10^{-5}$ degrees which is orders of magnitude better than previous methods.

An additional aspect of the present invention is to create a SPR sensor and detection method that is immune to ambient light, intensity fluctuations of the light source, and noise in the photo-detector and electronics.

A third aspect of the present invention is to modulate the SPR signal with the electrochemical potential of the metal film, for example using a lock-in technique, to improve the signal to noise ratio.

Another aspect of the present invention is to integrate electrochemical measurements, such as current, capacitance, and the like, into the SPR measurement, to provide important supplementary information about the detected molecules and improve specificity in the sensor and its applications. For example, since the ratio of the differential signal to the sum signal is proportional to the shift of the SPR angle, this method provides an accurate measurement of the SPR angle.

Yet another aspect of the present invention is to be able to miniaturize the SPR instruments and SPR-based sensors, which is important both for improving the thermal and mechanical stability of the instruments and sensor and for the convenience of using the instruments and sensors in a field environment. The SPR sensors based on the present invention are compact because they consist of only a focused light source, a prism and a photodetector, and high angular resolution is achieved without requiring a large sample-photodetector separation.

The above and other aspects, novel features, and advantages of the present invention will become apparent from the following detailed description of the preferred embodiments.

BRIEF DESCRIPTION OF THE DRAWINGS

In order that the invention may be better understood, several embodiments thereof will now be described by way of example only and with reference to the accompanying drawings in which.

FIGS. 4–10 illustrate the performance of which an arrangement in accordance with the invention is capable. Specifically:

FIG. 8($a$) is the cyclic voltammogram of cytochrome c immobilized on the surface of MPA coated gold electrode in 50 mM phosphate solution, as the electrode potential was scanned between −0.2 V and 0.3 V at a rate of 0.1 V/sec, where the arrows point to the oxidation and reduction of the protein, corresponding to the electron transfer reaction of the protein. FIG. 8($b$) is the corresponding dip shift in the SPR angle due to the oxidation and reduction.

FIG. 9($a$) is the absorption spectra of reduced (solid line) and oxidized (dashed line) cytochrome c. FIG. 9($b$) is the experimental SPR shift of cytochrome c (open and filled circles) as is switched from oxidized to reduced states. The kinks occur at absorption peaks, 550 nm and 520 nm. The shift in pure phosphate buffer (open squares). FIG. 9($c$) is the theoretical SPR shift based on the absorption peaks and the Kramers-Kronig relation.

DETAILED DESCRIPTION OF THE PREFERRED EMBODIMENTS

Figure 1:
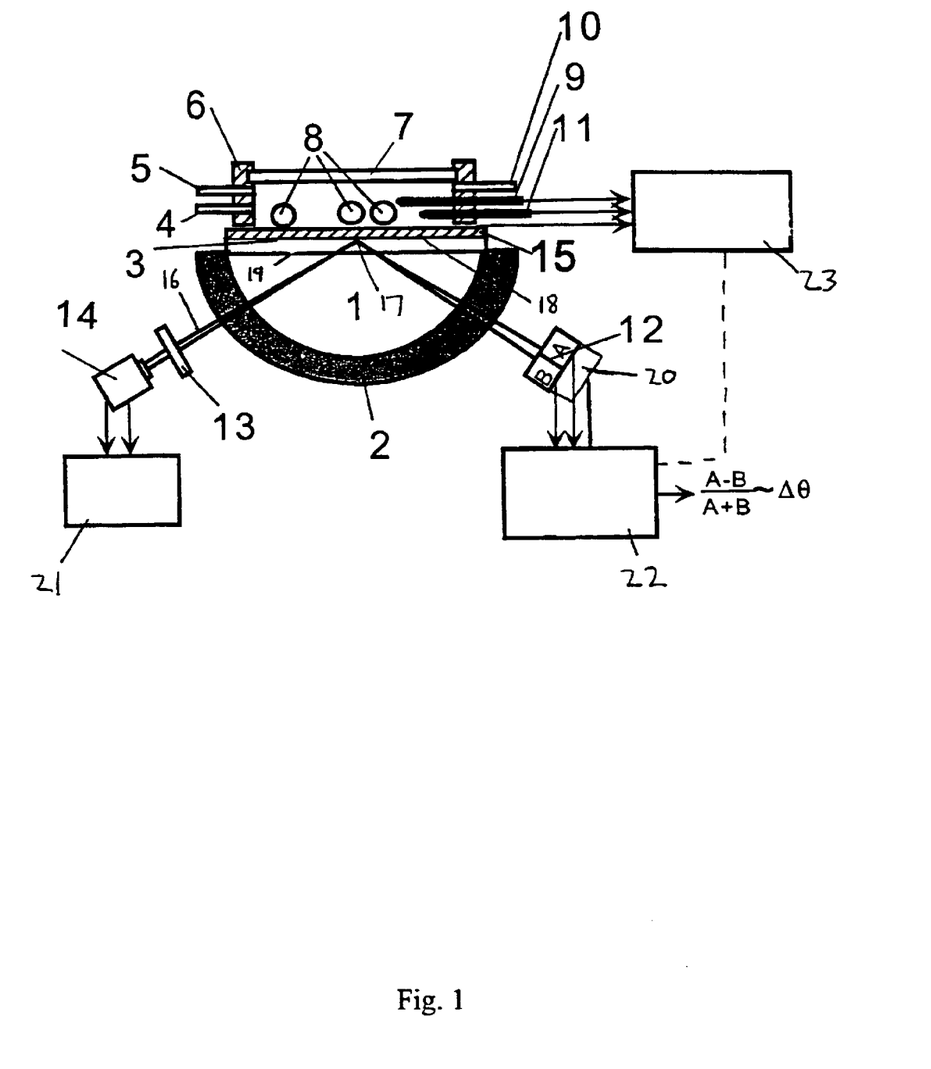
FIG. 1 is a schematic diagram of a cross-sectional view of the SPR sensor in accordance with one example of the invention.
Figure 2:
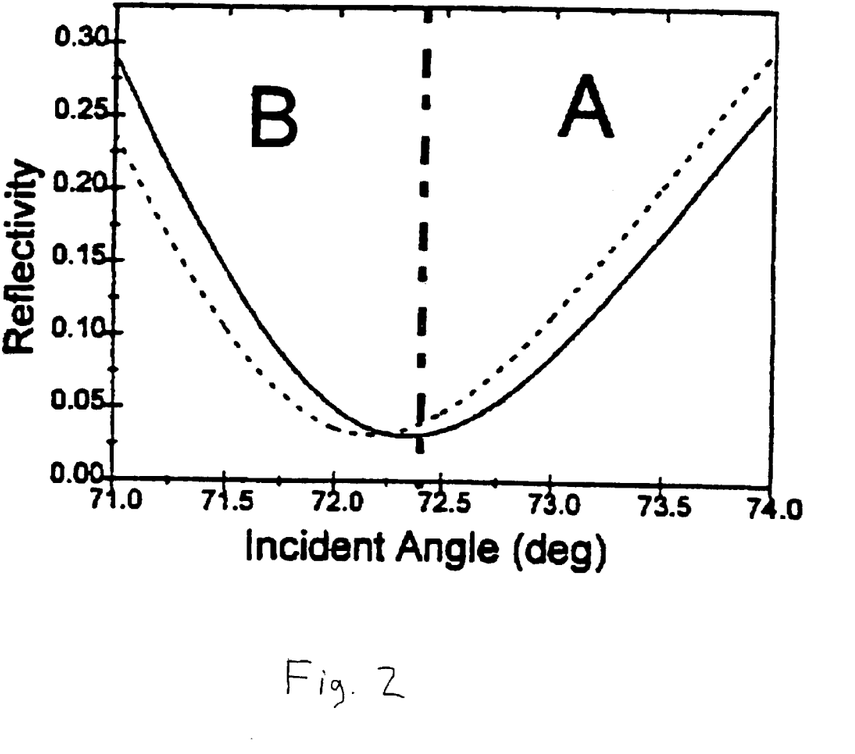
FIG. 2 is a intensity profile of the two cells of the differential position or intensity sensitive photo-detecting device before and after a shift in the SPR. The intensity of the two cells, A and B, is first balanced (area under the solid line). A shift in the SPR results in an intensity imbalance of the two cells (dashed lines) which is detected as the differential signal by the photodetector.

Referring to FIG. 1$a$, in one embodiment, the sensor comprises a collimated input beam 16 of electromagnetic radiation from a source 14, which may conveniently comprise an ordinary light source, with suitable filters and collimators, or preferably, a diode laser, or the like. The frequency of the radiation must be such as to result in the generation of surface plasmon waves and in practice will be within or near the visible region, although other frequencies are possible. Suitable sources include a 5 mW diode laser ($\lambda$=635 nm) such as that manufactured Hitachi. When a laser is used, it is controlled by a suitable laser controller, 21. The input beam, 16, is focused through a hemicylindrical (right-angle, or equilateral) focusing lens 13, made of a transparent material such as glass or quartz, with a focal length, $f_1$. This beam may optionally pass through other devices which change the properties of the beam such as a polarizer, a slit, additional lenses, or the like. The focusing lens focuses the light onto a point 17 on an interface 18 between an optically transmissive component, generally shown as 1 and 3, and a reflective layer in the form of a metal coating or film, 15.

The optically transmissive/transparent component is, in this example, made up of a thin support plate or slide-3, having a first sur ace (upon which the reflective layer is grown or coated,) and a hemispherical lens or prism 1 having a second, curved, spherical surface with its center of curvature located at the point 17. The optically transmissive component is usually made of glass. Any other geometry, shape, and size is possible for the optically transmissive component since any refraction which this component introduces can be ignored or compensated for. The arrangement is preferably such that all light rays in the convergent beam which emerges from lens 13 travel radially of the optically transmissive component 1 and 3 and thus undergo no refraction and are focused centrally on the point 17. The optically transmissive component 1 and 3 is attached by a supporting frame 2. The metal film material is commonly silver or gold, usually applied by evaporation. The film needs to be as uniform as possible in order to cater for minute movement in the point of incidence of the incoming beam. It is assumed that a structured metal film will give the best resonance and there are various ways well known in the art in which the optically transmissive component can be pretreated to improve the performance of the metal film and in particular to control the natural tendency of such films to form discontinuous islands. In the preferred embodiment the metal film 15 is eptaxially grown on the glass slide 3 which is placed onto the prism and optically coupled to the prism with a suitable index matching fluid or oil film, as shown at 19, between the facing surfaces of plate 3 and prism 1. In a practical realization of the invention, the metal layer 15 may be applied in any manner to the surface of the aforementioned slide 3.

Light internally reflected from the metal film at point 17 passes out of the slide and travels as a divergent, planar, fan-shaped beam that is detected with a radiation sensitive differential position or intensity sensitive photo-detecting device 12. The differential detecting device may comprise a large or small area detector, an array of detectors, or the like, for example, a mono- or big-cell photo-sensitive detector, or the like. For reasons of expense, compactness, and rapid response times, the use of a big-cell photo-sensitive detector is preferred. The differential detector generates electrical output signals indicative of the variation of intensity of light with position across the beam 16; the SPR effect dictating that strong absorption will occur at a particular angle as determined by material in the sample being tested. These electrical signals are sampled and digitized and fed via associated circuitry (not necessarily shown) to a suitable analyzing arrangement (collectively, 22) which may include a microprocessor or larger computer.

In one embodiment, a cell 6, made of a suitably inert material, for example Teflon, in which a sample of molecules is to be tested is placed is attached onto the metal film. A glass window 7 provides a view of the focused laser spot and also seals the solution from surrounding environment, which is important for air sensitive molecules. The cell has a port 5 for purging the solution with $N_2$, and two ports for counter 9 and reference 11 electrodes, which are needed for electrochemical control of the metal surface. It has also two additional ports 4, 10 of a size to allow the sample containing molecules to be tested to flow into the cell, contact the metal layer, and flow out of the cell, thus allowing the sample to be constantly replenished during the course of the test, which ensures maximum sensitivity. Other methods of feeding the sample are also possible. Any material whose refractive index may change may used as a sample, for example a molecule or molecules.

As the sample flows past the metal layer 15 the refractive index of layer 15 is altered/changes, which is monitored, optionally continuously, during the test. Provided that the angle of incidence at the point 17 is correct, the application of the light beam will result in the generation of a plasmon wave, thus extracting energy from the input beam and causing an attenuation or dip in the intensity of the output beam at a particular angle of incidence. The feedback circuitry monitoring the differential detecting device output enables the identification of the angle at which the reflectance dip can be obtained. This gives a highly sensitive output.

In one embodiment, the initial position or incident angle of the differential detecting device is adjusted via movable frame 20, for example a precision translation or rotation stage. The initial position is set up such that the difference in the photo signals (A–B) received from the differential detecting device 12, A–B is zero. This is usually the actual angle of the reflective dip which results before any sample is passed through the cell, or when some neutral, control, or buffer solution that the sample to be combined with is passed through the cell, or when the sample under test is passed through the cell, but before any reaction thereof has take place. Even as sample begins to flow past the metal layer, there is sufficient time to take a reading before the refractive index changes, which can be utilized to adjust and choose the correct position of the differential detecting device 12. When A–B is adjusted to zero, the reflectance dip is located near the center of the differential detecting device. The position of the detector can be manipulated by a variety of methods, preferably a stepping motor, which can be a component of 22. In another embodiment, the differential detection can be accomplished on a time basis rather than a positional or spatial basis.

In a further embodiment, the electrochemical potential of the metal film electrode is controlled and modulated with a potential control or modulator unit and/or potentiostat, 23. The response of the differential signal or (A–B)/(A+B) to the AC modulation of the electrochemical potential is detected with a lock-in amplifier as part of 22, which drastically improves the signal to noise ratio, therefore the angular resolution. While the amplitude information from the lock-in amplifier provides information on the SPR angle, the phase between the modulation and differential signal provides additional information about the response of the adsorbed molecules to the electrode potential. Both the DC and AC components of the corresponding current that flows between the metal film and a counter electrode are simultaneously measured with the SPR signal. The DC component provides the usual electrochemical characterization of molecules adsorbed onto the electrode. The AC component is used to extract interfacial capacitance, which provides supplementary information about the adsorbed molecules.

Figure 3:
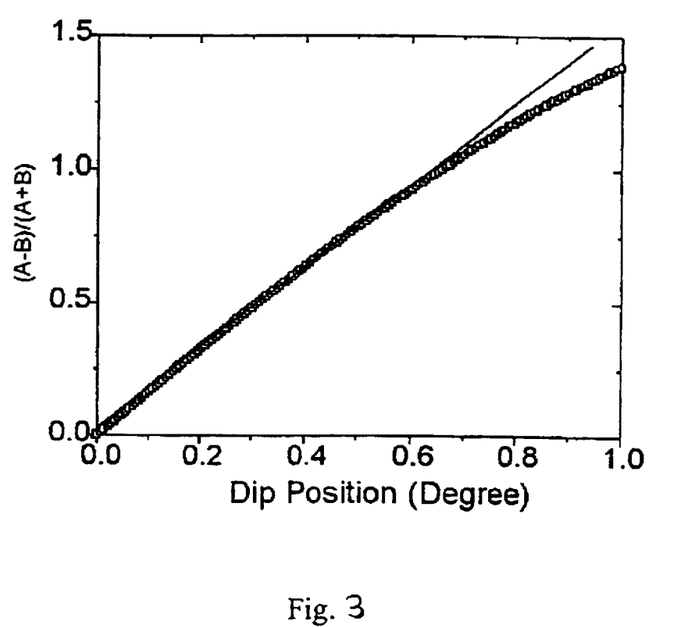
FIG. 3 is a theoretical simulation showing direct proportionality/a linear relationship between the ratio of the differential signal to the sum/total signal of the differential position or intensity sensitive photo-detecting device, (A−B)/(A+B), and the actual SPR dip position over a large angular range.
Figure 4:
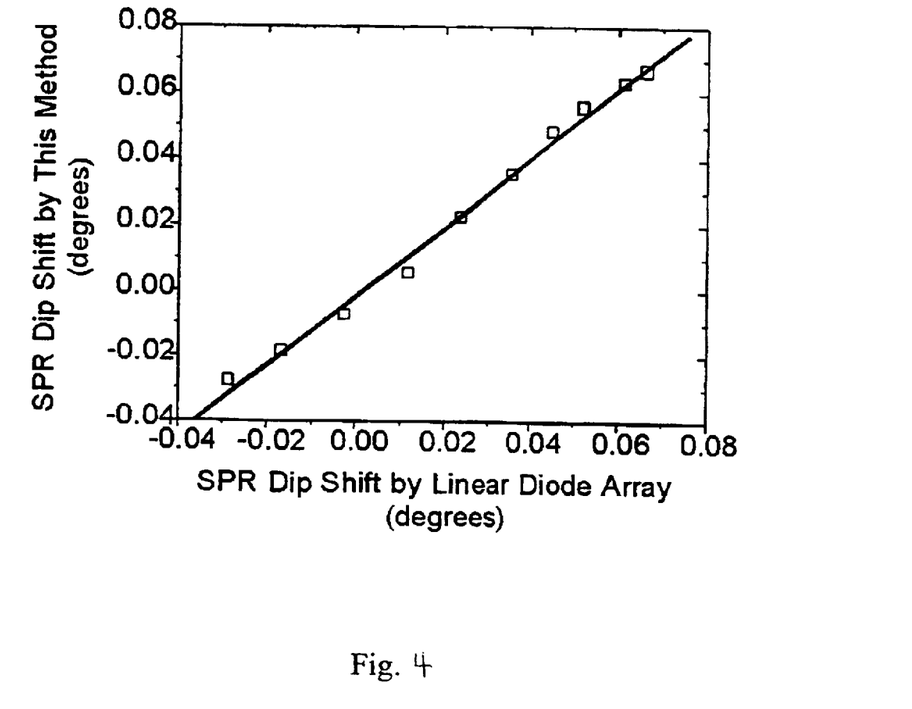
FIG. 4 is a experimental calibration of the SPR dip position of a gold film in phosphate buffer at various potentials measured by this method vs. the dip position of the same sample measured with a conventional diode array setup, showing excellent agreement between the two methods.

FIG. 3 is a theoretical simulation showing a linear relationship between the ratio of the differential signal to the sum signal of the photodetector, (A–B)/(A+B), and the actual SPR dip position over a large angular range. The simulation was performed using a matrix method (W. N. Hansen in Journal of Optical Society of America, 1969). The slope is about 1.5. Assuming that the reflectivity near the dip position over a small angular range is parabola, the ratio of the differential signal (A–B) to the total signal (A+B) expressed as (A–B)/A+B) is proportional to the shift of the SPR dip position with slope of 2 for an angular range of 3 degrees. The slope is somewhat greater than 1.5 because of the dip shape is not exactly a parabola FIG. 4. is a experimental calibration of the SPR dip position of a gold film in phosphate buffer at potentials between measured by the sensor of this invention by the method of this invention vs. the dip position of the same sample measured with a conventional diode array setup, showing excellent agreement between the two methods.

As will be appreciated from the foregoing description, the response time of the sensor of this invention and the method of this invention is limited only by the characteristics of the differential detecting device and its associated sampling and computing circuits. A prototype setup has achieved response times in the range of a few $\mu$s, limited only by the bandwidth of a nonintegrated preamplifier. Commercially available integrated preamplifiers provide a response time in the range of a few picoseconds. These ultrafast response times enables initial transients and other shifts which may occur during the test or analysis to be monitored and allowed for and also permits rapid calibratory checks to be made. The present invention enables the desired reflectivity characteristic to be determined on a time scale so short that it is less than the time taken for chemical bonding to be achieved between the relevant constituent of the sample and the reflective layer.

Figure 5:
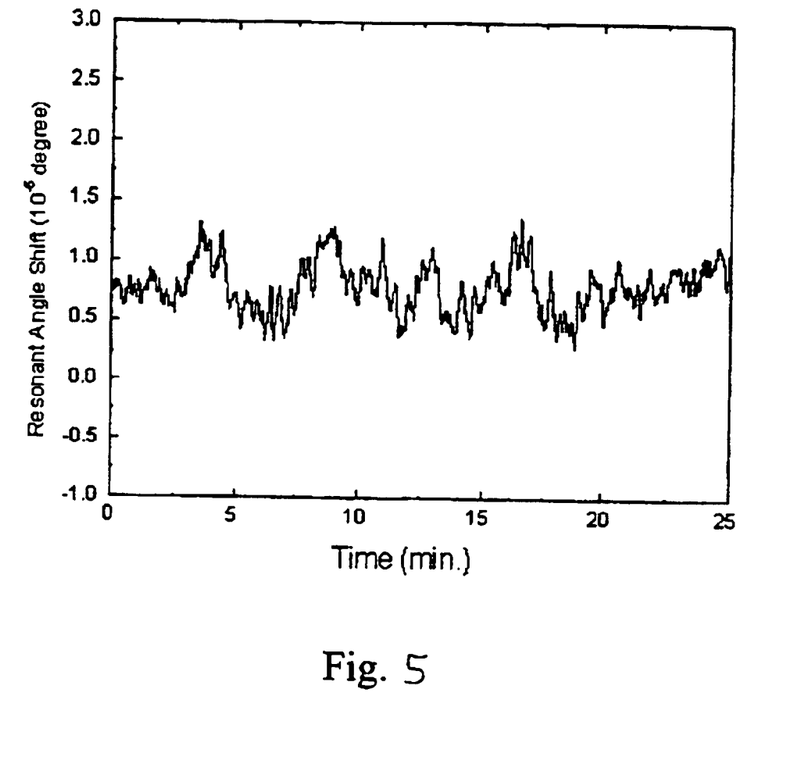
FIG. 5 is a typical SPR shift due to thermal drift and mechanical vibrations in a prototype setup based on the present invention.

The sensor of the present invention can be made very compact, which advantageously results in great reduction in noise due to thermal drift and mechanic vibrations. In contrast, high resolution in prior art sensors requires a large distance between the photodetector and the sample. A prototype setup that has an angular range of 1.8 degrees and a band width of 100 Hz has achieved an angular resolution on the order of $10^{-5}$ degrees (FIG. 5). To achieve the same resolution with the diode array or CCD detector setup, the distance between sample and detector would have to be on the order of hundreds of meters. Since the resolution is inversely proportional to the angular range, higher resolutions can be achieved with a smaller angular range. Using a 3 mW laser and a commercial photodetector that has a noise equivalent power (NEP) of $10^{-14}$ W/Hz$^{1/2}$, the resolution would be expected to be in the range of $10^{-8}$ degrees for a bandwidth of 100 Hz with an angular range of 3 degrees. The high resolution, fast response times, and compact design of the present invention allows for a wide variety of applications in the fields of biology, biochemistry, and chemistry.

In addition to high resolution, fast response time, and compact design, the differential detection method in this invention makes the system immune to the disturbing effects of extraneous light such as room light and also minimizes the problem due to unavoidable fluctuations in the intensity of the light source and other common noise. This avoids the expense and inconvenience of shrouding the entire or particular components of the arrangement, modulating the light source, or tuning the detectors and/or the processing circuits to a particular response.

The following examples are provided to further illustrate specific aspects and practices of this invention. These examples describe particular embodiments of the invention, but are not to be construed as limitations on the scope of the present invention or the appended claims.

EXAMPLE 1

SPR Setup 1

In one SPR setup, a BK7 plano-cylindrical lens (Melles Griot) was used as a prism. The prism is close to but not exactly hemicylindrical. On the prism, a 50 nm thick gold film evaporated on a BK7 glass slide in ultrahigh vacuum was placed with an index matching fluid. The gold film was annealed in a hydrogen flame briefly before each experiment in order to reduce surface contamination. A 5 mW diode laser (1=635 nm, Hitachi), driven with a homemade laser controller, was collimated and then focused by a 14 mm local-length lens through the prism onto the gold film. Light reflected from the gold film was detected with a bicell photodiode detector (Hamamatsu Corp., model S2721-02) which was mounted on a precision translation stage. The photocurrents from the two cells (A and B) were converted to voltages with a homemade circuit. The circuit also calculated the differential, A–B, and the sum, A+B, signals which were then sent to a PC computer equipped with a 16 bit data acquisition board (National Instrument). For fast kinetic studies, the differential and sum signals were sent to a 150 MHZ digital oscilloscope (Yokogawa, DL 1520L). Before each measurement the prism was rotated so that there was a dark line located at the center of the laser beam. The dark line is due to the adsorption of the light by the surface plasmon which occurs at the angle of resonance. The reflected light falling onto the two cells of the photodetector was then balanced by adjusting the photodetector position with the translation stage until A–B approached zero. Because of the high sensitivity of the method, drift in the A–B signal due to mechanical stress was clearly visible immediately after alignment but it settled down typically over a period of 15–30 min when all the screws were properly tightened. The ratio of the differential to sum signals, which is linearly proportional to the SPR angular shift was obtained numerically by dividing A–B with A+B.

On the gold film a Teflon sample cell was mounted to hold sample solutions. The cell has two ports for flowing sample solution in and out, and a port for purging $O_2$ out of the solution with $N_2$, or another suitable inert gas, which is necessary for many experiments. To control the electrochemical potential of the gold film electrode, Pt and Ag wires were used as counter- and quasireference electrodes, respectively. The quasireference electrode was calibrated against a Ag/AgCl reference electrode. The electrochemical potential of the gold film was controlled with an EG&G model 283 potentiostat.

EXAMPLE 2

SPR Setup 2

An alternate SPR setup used a BK7 plano-cylindrical lens (Melles Griot) as a prism. On the prism, a BK7 glass slide, coated with a 45 nm thick silver or gold film by a sputtering coater, was placed with an index matching fluid. White light from a 150 W xenon lamp (Oriel) was sent to a monochromator. Monochromatic light with a bandwidth of ca. 0.5 nm from the monochromator was collimated and then focused by a 14 mm focal-length lens through the prism onto the silver film. Light reflected from the silver film was detected with a bi-cell photodiode detector (Hamamatsu Corp., model S2721-02), which was mounted on a precision translation stage. In each measurement the prism was rotated such that a dark line, corresponding to the SPR dip, was located at the center of the laser bean. The reflected light falling onto the two cells of the photodetector was then balanced by adjusting the photodetector position with the translation stage until the differential signal approached zero. The shift in SPR angle is proportional to the differential angle, which was precisely measured. The response of the differential signal to the modulation of the electrode potential as a function of 1 was recorded with a lock-in amplifier (Princeton Applied Research, Model 5110). The output form the lock-in amplifier normalized by the sum signal of the photodetector is proportional to $\Delta\theta(\lambda)/\Delta V$, which was used to calculate Stark spectrum $\Delta\epsilon/\Delta V$, according to the Kramers-Kronig relation.

On the silver film a Teflon sample cell was mounted to hold sample solutions. In order to control the electrode potential, Pt and Ag wires were used as counter and quasireference electrodes, respectively, with a Potentiostat (Pine Instruments). The quasireference electrode was calibrated with respect to Ag/AgCl (in 3M KCl) reference electrode. The experiments were conducted with the electrode being held at 0.2 V with a ca. 10 mV modulation at 200 Hz was applied to the potential. The potential was chosen such that no electrochemical reactions take place on the silver film.

EXAMPLE 3

Effects of Electron Density on SPR

Figure 6:
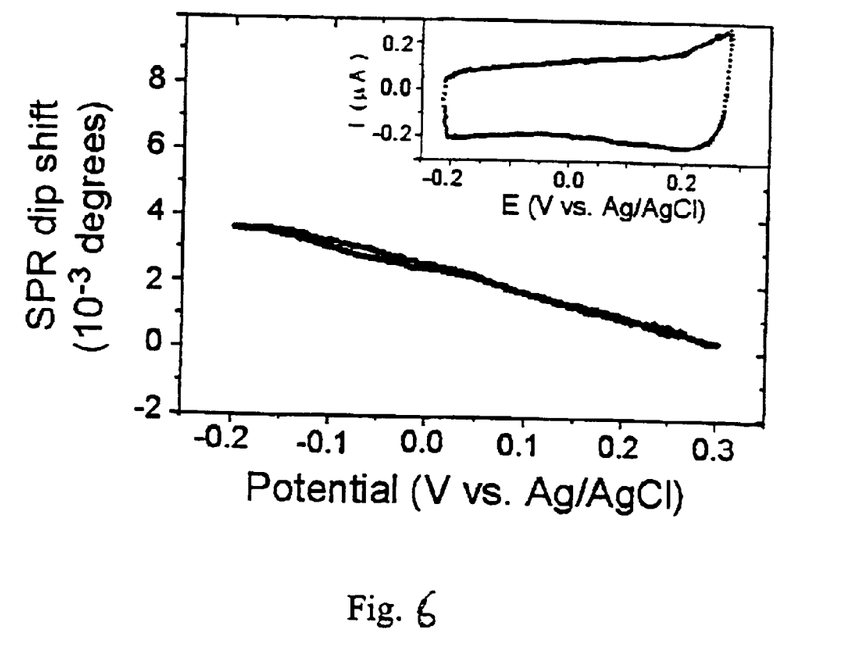
FIG. 6 is a SPR dip shift of mercaptoproprionic acid (MPA)-coated gold electrode in 50 mM phosphate solution as the electrode potential is scanned between −0.2 V(vs. Ag/AgCl reference electrode) and 0.3 V at a rate of 0/1 V/sec. The inset shows the simultaneously recorded cyclic voltammogram.

FIG. 6 shows the SPR dip position of a gold film (electrode) coated with an organic monolayer (mercaptopropionic acid or MPA) in 50 mM phosphate buffer as the electrode potential was varied linearly from –0.2 V to 0.3 V (v.s. Ag/AgCl). The dip position shifts about 0.0008 degrees per 100 mV which is too small to be easily detected with a conventional SPR setup. It has been recognized that electrode potential can change the SPR dip position via changing the electron density in the metal film. The shift observed here is much smaller than that for a bare gold electrode because the presence of MPA decreases the surface capacitance therefore the electron density change for a given potential change.

EXAMPLE 4

Protein Adsorption Onto Self-assembled Monolayers

Figure 7:
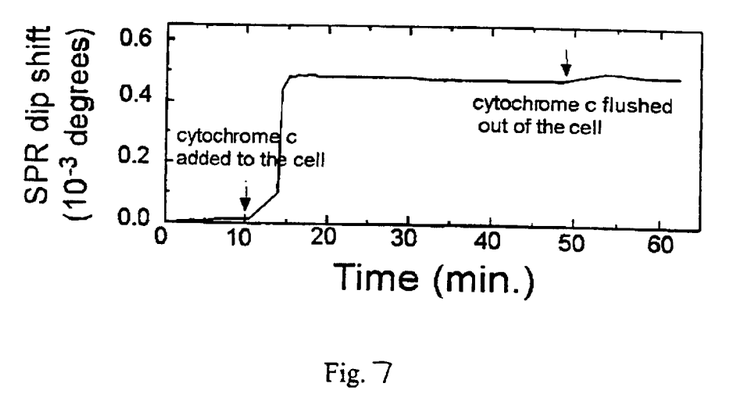
FIG. 7 is a SPR dip shift as a function of time before, during and after redox protein, cytochrome c, was introduced into the solution cell. The two arrows mark the moments when the cytochrome c was introduced and the cytochrome c solution was replaced with buffer, respectively.

FIG. 7 shows the adsorption process of cytochrome protein onto 3mercaptopropionic acid-coated gold electrode monitored by the SPR. The measurement was started with monitoring the SPR dip position in a buffer solution in which no protein was present. Then a 20 µL 27 µM horse heart cytochrome c (Cytc, purchased and used without further purification from Fluka) +50 mM phosphate (pH 6.4) was injected into the solution cell via the solution port in the cell and subsequent SPR dip position was monitored continuously. The dip position increased and reached a stable value in about 15 minutes. Replacing the Cytc solution with buffer solution, the dip position did not change back, showing at the adsorbed protein was rather stable on the surface.

EXAMPLE 5

Electron Transfer-induced Conformational Change in Redox Proteins

Figure 8:
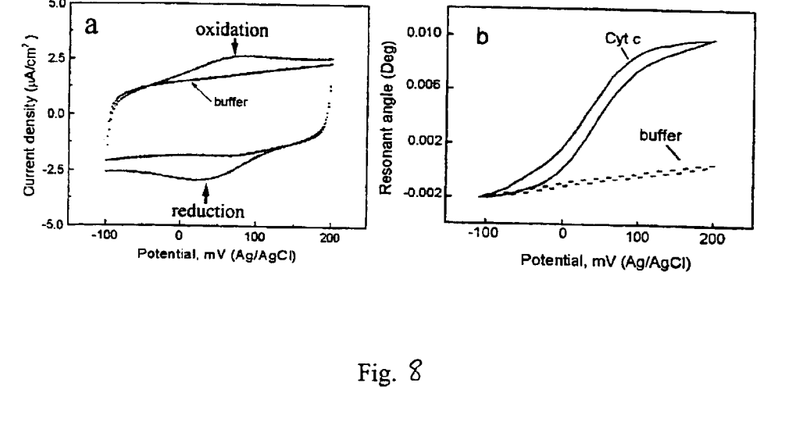

In the presence of adsorbed Cytc on the electrode surface, the change of the electrode potential can trigger an electron transfer between the electrode and the adsorbed protein via oxidation and reduction. This electron transfer is shown in the concurrently measured cyclic voltammogram as a pair of peaks (FIG. 8a). The measured SPR dip position shows a sigmoid increase when switching the protein from the oxidized to the reduced states (FIG. 8b). The change, which is about 0.006 to about 0.01 degrees, is reversible when switching the protein back to the oxidized state. Note that the error in the change is primarily from the uncertainty in determining the background SPR shift, rather than the SPR setup. The SPR shift can be attributed to a conformational change in the protein induced by the electron transfer reaction. This change can affect both the thickness and the index of refraction of the protein layer. According to Lorentz-Lorentz relation, the change in the index of refraction ($\Delta n$) of the protein layer is related to the thickness $\Delta d$ by $\Delta n/n=-(\frac{1}{6})(1-1/n^2)(2+n^2)\Delta d/d$, where n and d are the index of refraction and thickness of the protein layer, respectively. Using the relation, we have estimated that 0.006°–0.01° increases in the dip angle as Cytc transforms from oxidized to reduced states corresponds to ca. 0.3 Å decreases in the thickness.

EXAMPLE 6

Multi-wavelength SPR.

Figure 9:
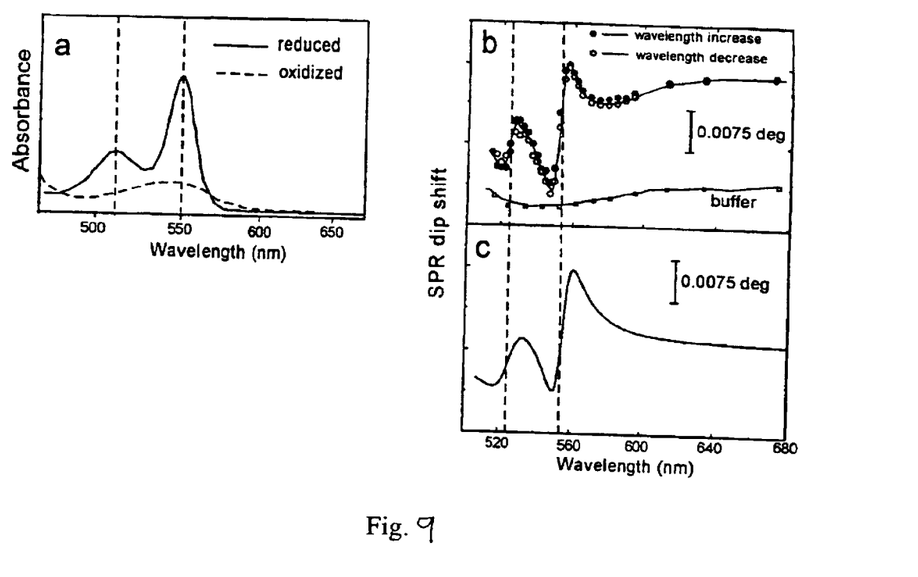

The capabilities of absorption spectroscopy can be integrated into SPR with the use of multi-wavelength incident light. The working principle is base on the Kramers-Kronig relation that relates the refractive index of the molecules measured by SPR to absorption coefficient by absorption spectroscopy. Using the differential method disclosed here, multi-wavelength SPR can be applied to the electron transfer reaction of cytochrome c. The wavelengths between 500 nm and 700 nm were scanned because the reduced cytochrome c (solid line) has two pronounced absorption peaks at 520 nm and 550 nm, while the oxidized cytochrome c (dashed line) is relatively flat in the wavelength window (FIG. 9a). The measured shift in the resonant angle vs. wavelength is plotted in FIG. 9b. Far away from the absorption peaks, the shift does not depend much on the wavelength and it measures a conformational change in the protein. However, when the wavelength is close to the absorption peaks, two interesting kinks centered at 520 nm and 550 nm appear, as expect from the Kramers-Kronig relation. Using the absorption spectra at inputs, we have calculated the SPR dip shift (FIG. 9c) using the KramersKronig relation and found a quantitative agreement between the theory and the experimental data (FIG. 9b).

EXAMPLE 7

The Kinetics of Conformational Change in Proteins

Figure 10:
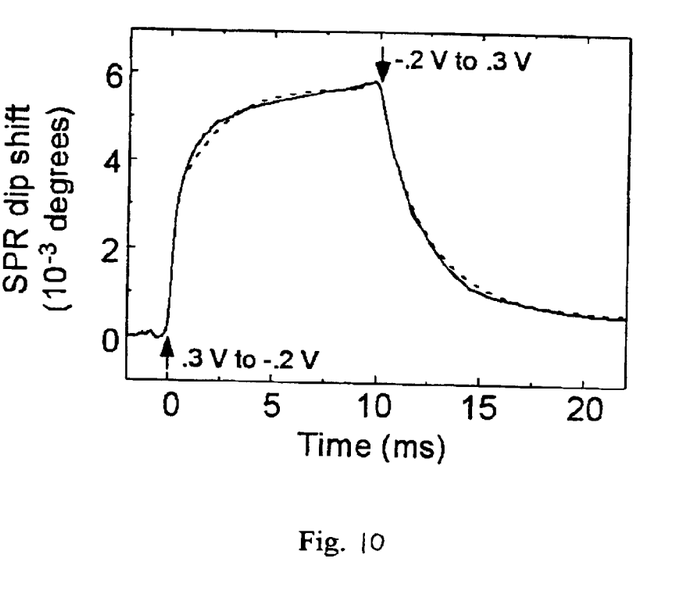
FIG. 10 shows the kinetics of the electron transfer induced conformational change in cytochrome c immobilized on MPA-coated gold electrode in 50 mM phosphate buffer. The response of the SPR dip position was obtained when stepping the potential from 0.3 to −0.2 V and back to 0.3 V after staying at −0.2 V for 10 ms. The dashed lines are fittings with simple exponential functions.

The kinetics of the above electron transfer induced-conformational change has been probed by taking advantage of the fast response time of the present SPR setup. FIG. 10 shows the response of the SPR dip position as the potential was suddenly stepped from 0.3 V, where the protein was in the oxidized state, to −0.2 V, where the protein transformed into the reduced state. The potential was held at −0.2 V for various time intervals before being stepped back to 0.3 V. The shortest time that could be studied was limited by the response time of the electrochemical cell rather than by the SPR setup. Over the time window shown in FIG. 10, the SPR response can be roughly fitted by an exponential function with a time constant of ca. 2.1 ms for reduction and ca. 2.5 ms for oxidation . The change due to reduction is faster than that of oxidation. This observation is consistent with the previous studies that Cytc in the reduced state is more stable than that in the oxidized state.

The above examples demonstrate the novelty and utility of the high-resolution SPR sensor and method of the present invention. Every reference cited herein is hereby incorporated by reference in its entirety. The foregoing detailed description of the preferred embodiments of the invention has been given for clearness of understanding only, and no unnecessary limitations should be understood therefrom, as modifications will be obvious to those skilled in the art. Variations of the invention as hereinbefore set forth can be made without departing from the scope thereof and, therefore, only such limitations should be imposed as are indicated by the appended claims.

What is claimed is:

1. A method of detecting surface plasmon resonance comprising the steps of:
   (a) focusing a beam of electromagnetic radiation on a layer of metallic material, upon which layer is optionally a sample material;
   (b) detecting said beam of electromagnetic radiation reflected from said layer of metallic material with a differential position or intensity sensitive photo-detecting device;
   (c) noting the intensity of the first A position or intensity signal and the intensity of the first B position or intensity signal produced by said differential position or intensity sensitive photo-detecting device;
   (d) positioning said differential position or intensity sensitive photodetecting device such that the surface plasmon resonance intensity minimum is near the center of the differential position or intensity sensitive photo-detecting device such that the difference in said A position or intensity signal and said B position or intensity signal is near zero;
   (e) detecting subsequent changes in the intensity distribution due to the surface plasmon resonance angular shift; and
   (f) amplifying the differential signal received from said differential position or intensity sensitive photo-detecting device.

2. A method of detecting surface plasmon resonance in accordance with claim 1, wherein said differential position or intensity sensitive photodetecting device is a bi-cell photodetector, wherein one cell produces said A position or intensity signal and the other cell produces said B position or intensity signal.

3. A method of detecting surface plasmon resonance in accordance with claim 1, wherein said differential position or intensity sensitive photo-detecting device is a mono-cell photodetector that produces both said A and B position or intensity signals by sampling intensity at alternate time points.

4. A method in accordance with claim 1, wherein said amplifying the differential signal can be adjusted or varied.

5. A method in accordance with claim 1 further comprising the step of determining said differential signal, a sum signal, and a ratio of said differential signal to said sum signal.

6. A method in accordance with claim 5 where said amplifying a differential signal and determining said differential signal, a sum signal, and a ratio of the differential signal to the sum signal is done by an electronic unit.

7. A method in accordance with claim 5 further comprising the step of modulating/controlling the electrochemical potential of the layer of metallic material.

8. A method in accordance with claim 7 wherein said modulating the electrochemical potential of the layer of metallic material is done by at least one reference electrode and at least one counter electrode.

9. A method in accordance with claim 8, wherein said reference electrode (s) and counter electrode (s) are elements of a means of introducing onto said layer of metallic material a sample to be analyzed.

10. A method in accordance with claim 1, wherein said amplifying the differential signal can be done to the extent such that there is substantially no problem of saturation.

11. A method in accordance with claim 7 further comprising the step of detecting the SPR angle and the electrochemical current.

12. A method in accordance with claim 11, wherein said detecting the SPR angle and the electrochemical current is done by at least one lock-in amplifier.

13. A method in accordance with claim 7, wherein said detecting the SPR angle and the electrochemical current functions concurrently with the modulation of the electrochemical potential of the layer of metallic material.

14. A method in accordance with claim 1, further comprising the step of determining interfacial capacitance.

15. A sensor in accordance with claim 14, wherein said determining interfacial capacitance consists of simultaneously recording the DC and AC components of the electrochemical current.

16. A method in accordance with claim 14, further comprising the step of simultaneously recording the amplitude and phase of the differential signal.

17. A sensor comprising:
(a) a sensor body made of a material transparent to electromagnetic radiation;
(b) a layer of metallic material disposed over at least part of a first surface of said body;
(c) apparatus for mounting a sample to be analyzed onto to said layer of metallic material;
(d) a source of a beam of electromagnetic radiation for focusing on said layer of metallic material;
(e) a differential position or intensity sensitive photo-detecting device responsive to a beam of electromagnetic radiation reflected from said layer of metallic material;
(f) apparatus for varying the position of said differential position or intensity sensitive photo-detecting device; and,
(g) apparatus for amplifying a differential signal received from said differential position or intensity sensitive photo-detecting device such that the difference in the intensity signal received is near zero.

18. A sensor in accordance with claim 17, wherein said differential position or intensity sensitive photo-detecting device consists of at least one photo-cell.

19. A sensor in accordance with claim 17, wherein said differential position or intensity sensitive photo-detecting device consists of at least two photo-cells.

20. A sensor in accordance with claim 17, wherein said means for introducing onto said layer of metallic material a sample to be analyzed is a sample cell comprising:
(a) a sample cell body of a material that isolates said sample from ambient air;
(b) a window in said sample cell body of a material that is transparent to electromagnetic radiation; and,
(c) at least one port for introducing and removing said sample.

21. A sensor in accordance with claim 17, wherein said means for amplifying a differential signal can be adjusted or varied.

22. A sensor in accordance with claim 17, further comprising a means for determining said differential signal, a sum signal, and a ratio of said differential signal to said sum signal.

23. A sensor in accordance with claim 22, where said means for amplifying a differential signal and means for determining said differential signal, a sum signal, and a ratio of the differential signal to the sum signal is an electronic unit.

24. A sensor in accordance with claim 22 further comprising a means for modulating/controlling the electrochemical potential of the layer of metallic material.

25. A sensor in accordance with claim 24 wherein said means for modulating the electrochemical potential of said layer of metallic material consists of at least one reference electrode and at least one counter electrode.

26. A sensor in accordance with claim 25, wherein said a means of introducing onto said layer of metallic material a sample to be analyzed includes said reference electrode (s) and counter electrode(s).

27. A sensor in accordance with claim 17, further comprising a means to bring said differential signal near zero prior to measurement such that the differential signal can be amplified to the extent such that there is substantially no problem of saturation.

28. A sensor in accordance with claim 27, wherein said means to bring the differential signal near zero prior to measurement consists of mounting said differential position or intensity sensitive photo-detecting device on a movable part that can be positioned such that the differential signal that said differential position or intensity sensitive photo-detecting device detects is near zero prior to measurement.

29. A sensor in accordance with claim 17 further comprising a means for detecting SPR angle and electrochemical current from the metallic material or molecules associated with the metallic material.

30. A sensor in accordance with claim 29, wherein said means for detecting the SPR angle and the electrochemical current consists of at least one lock-in amplifier.

31. A sensor in accordance with claim 24, wherein said means for detecting the SPR angle and the electrochemical current functions concurrently with the modulation of the potential of the layer of metallic material.

32. A sensor in accordance with claim 17, further comprising a means of determining interfacial capacitance.

33. A sensor in accordance with claim 32, wherein said means of determining interfacial capacitance consists of a means of simultaneously recording the DC and AC components of the electrochemical current.

34. A sensor in accordance with claim 31, further comprising a means of simultaneously recording the amplitude and phase of the differential signal.

35. A sensor in accordance with claim 17 which is less than 2 inches in dimension.

36. A method comprising utilizing a sensor in accordance with claim 17, in biological, biochemical, or chemical testing.

37. A method of determining the surface plasmon resonance angle using a sensor in accordance with claim 17, comprising the steps of:
(a) determining the differential signal;
(b) determining the sum signal;
(c) determining the calibration curve;
(d) determining the ratio of the differential signal to the sum signal based on the calibration curve.

* * * * *

UNITED STATES PATENT AND TRADEMARK OFFICE
CERTIFICATE OF CORRECTION

PATENT NO. : 6,784,999 B1
DATED : August 31, 2004
INVENTOR(S) : Nongjian Tao et al.

It is certified that error appears in the above-identified patent and that said Letters Patent is hereby corrected as shown below:

Title page,
Item [57], ABSTRACT,
Line 18, replace "light," with -- light. --.

Column 14,
Line 14, replace "said a means" with -- said means --.
Lines 31-32, replace "comprising a means" with -- comprising means --.
Lines 40-41, replace "of the potential" with -- of the electrical potential --.
Lines 55 and 58, replace "claim 17," with -- claim 17 --.

Signed and Sealed this

Nineteenth Day of April, 2005

JON W. DUDAS
*Director of the United States Patent and Trademark Office*